United States Patent
Mosbach et al.

(10) Patent No.: US 7,087,748 B2
(45) Date of Patent: Aug. 8, 2006

(54) PROCESS

(75) Inventors: Klaus Mosbach, Lund (SE); Lei Ye, Lund (SE); Yihua Yu, Lund (SE)

(73) Assignee: SmithKline Beecham P.L.C., Brentford (GB)

(*) Notice: Subject to any disclaimer, the term of this patent is extended or adjusted under 35 U.S.C. 154(b) by 0 days.

(21) Appl. No.: 10/380,686

(22) PCT Filed: Sep. 17, 2001

(86) PCT No.: PCT/EP01/10742

§ 371 (c)(1),
(2), (4) Date: Oct. 10, 2003

(87) PCT Pub. No.: WO02/22846

PCT Pub. Date: Mar. 21, 2002

(65) Prior Publication Data

US 2004/0063930 A1 Apr. 1, 2004

(30) Foreign Application Priority Data

Sep. 18, 2000 (GB) .................................. 0022841.1

(51) Int. Cl.
*C07D 503/18* (2006.01)

(52) U.S. Cl. ...................................... 540/349; 525/259

(58) Field of Classification Search .................... None
See application file for complete search history.

(56) References Cited

U.S. PATENT DOCUMENTS 5,780,274 A * 7/1998 Capuder ...................... 435/119
5,821,364 A * 10/1998 Weber ......................... 540/349
5,985,625 A * 11/1999 Capuder ...................... 435/119

FOREIGN PATENT DOCUMENTS

| EP | 0 182 522 | 5/1986 |
| EP | 0 867 515 | 9/1998 |
| WO | WO 93/05068 | 3/1993 |
| WO | WO 97/08175 | 3/1997 |
| WO | WO 98/23622 | 6/1998 |
| WO | WO 98/42858 | 10/1998 |

OTHER PUBLICATIONS

Lei Ye, et al Biotechnology and Bioengineering vol. 64, Issue 6, (1999) pp. 650-655.*
J. Y. Ju, et al., Biotechnology and Bioengineering vol. 64, Issue 2 (1999) pp. 232-239.*
Maria Kempe et al., Journal of Chromatography A, vol. 694, Issue 1 , Mar. 3, 1995, pp. 3-13 □□.*
Maria Kempe, Journal of Molecular Recognition vol. 8, Issue 1-2 (1995) pp. 35-39□□.*

* cited by examiner

*Primary Examiner*—Mark L. Berch
(74) *Attorney, Agent, or Firm*—William T. Han; Edward R. Gimmi; Charles M. Kirzig

(57) ABSTRACT

A novel process for the removal of impurities from clavulanic acid using a selective adsorption material, in particular a molecularly imprinted polymer. Novel selective adsorption materials suitable for the process, and a process for the preparation of such selective adsorption materials, are also disclosed.

6 Claims, 3 Drawing Sheets allylamine 2-(diethylamino)ethyl methacrylate 1-(2-aminoethyl)-methacrylamide 2-(trimethylamino)ethyl methacrylate N,N'-diethyl-4-styrylamidine urocanic ethyl ester

PROCESS

The present invention relates to a novel process for the preparation of clavulanic acid or a pharmaceutically acceptable salt thereof in a purer form, to a selective adsorption material used therein and to a process for the preparation of such selective adsorption materials.

Clavulanic acid (Z)-(2R,5R)-3-(2-Hydroxyethylidene)-7-oxo-4-oxa-1-azabicyclo[3.2.0]heptane-2-carboxylic acid), that is to say, the compound of formula (I):

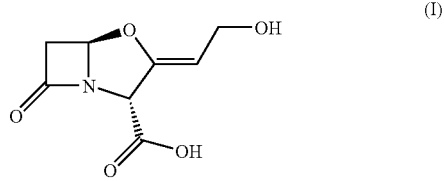

is known in the art as a β-lactamase inhibitor and which is used commercially as a component of pharmaceutical formulations, usually in the form of its pharmaceutically acceptable salts such as potassium clavulanate. Clavulanic acid is produced commercially by culture of the microorganism *Streptomyces clavuligerus*, for example by methods as described in GB-A-1 508 977.

Clavulanic acid may be extracted from the culture medium in various ways. Normally the cells of the *S. clavuligerus* are first removed from the culture medium by such methods as filtration or centrifugation before such extraction procedures are commenced. The clavulanic acid may be extracted from this clarified culture medium by solvent extraction from cold clarified culture medium adjusted to an acid pH. In the solvent extraction process the clavulanic acid is extracted into an organic solvent. After separation of the phases clavulanic acid is found in solution in the organic phase.

The clavulanic acid may be back extracted from the organic phase into a new aqueous phase by making use of the greater water solubility of salts of clavulanic acid with organic amines, and isolating such an amine salt from the aqueous phase. In such a process the amine salt is formed as an intermediate in the process of converting crude clavulanic acid into a pharmaceutically acceptable salt. Such a process is described in for example EP-A-0 026 044, in which a solution of impure clavulanic acid in an organic solvent is contacted with t-butylamine to form the t-butylamine salt of clavulanic acid, which is then isolated. Other similar processes are known which use other organic amines, such as tertiary octylamine (see EP-A-0 594 099 (Pharma Development)) diethylamine, tri-(lower alkyl) amines, dimethylaniline and NN'-diisopropyl-ethylenediamine. WO-A-93/25557 (SmithKline Beecham) discloses a very extensive list of amines which can be used in this way. WO-A-94/22873 (Gist Brocades) discloses use of various tertiary, tertiary diamines such as N,N,N',N'-tetramethyl-1,2-diaminoethane, N,N,N',N'-tetramethyl-1,6-diaminohexane, 1,2-dipiperidinoethane and dipiperidinomethane. WO-A-96/20199 (Spurcourt) discloses use of diaminoethers such as bis (2-dimethylaminoethyl) ether. GB-A-2 298 201 (Spurcourt) discloses use of various benzhydrylamines. WO-A-96/33197 (LEK) discloses use of further amines including symmetrical N,N'-alkylethylene diamines, such as N,N'-diisopropyl-ethylenediamine, N,N'-diethylene diamine, N,N'-dibenzylethylene diamine and N,N,N',N'-tetramethylene diamine. WO-A-98/21212 (Gist-Brocades) for example discloses a process in which the amines N,N,N',N'-tetramethylethylenediamine, 1,3-bis(di-methylamino)-2-propanol, benzhydrylamine and bis (2-(dimethylamino)ethyl) ether are used. WO-A-98/23622 (Biochemie) discloses use of diisopropyl-ethylene-diamine.

After isolation the intermediate amine salt may be converted into a pharmaceutically useful salt of clavulanic acid, particularly an alkali metal salt especially potassium clavulanate, generally by reaction of the intermediate amine salt with a salt precursor compound such as potassium 2-ethylhexanoate.

The above-discussed processes by which clavulanic acid and its pharmaceutically acceptable salts are prepared gives rise to certain side products, metabolites and degradants (hereafter known as impurities). A number of such impurities have been identified as peaks in the HPLC trace of crude clavulanic acid, intermediate amine salts and pharmaceutically acceptable salts of clavulanic acid. Some of these impurities have subsequently been chemically identified. Clearly, it is desirable that the level of such impurities in the final product is kept to a minimum. There is therefore a requirement for a new process for selectively removing known clavulanic acid impurities, that works in conjunction with known purification techniques and is capable of being utilised on a commercial scale.

A process termed "molecular imprinting" is also known, being a technique for preparing polymers that are selective adsorbant materials for a particular compound ("the print molecule"). The technique involves co-polymerising one or more monomers which are capable of binding the print molecule, with an excess of a cross-linking monomer, in the presence of the print molecule, typically also with an initiator to initiate polymerisation. Removal of the print molecule from the so-formed polymer, e.g. by extraction or chemical cleavage, leaves binding groups correctly immobilised in space and present in cavities which have the same shape of a mould of the print molecule, that "remember" the shape and functionalities of the print molecule. Polymerisation thus preserves the complementarity to the print molecule and the so-formed polymer, termed herein a "molecularly imprinted polymer" will subsequently selectively adsorb the print molecule, and the print molecule binds more favourably to the extracted polymer than do structural analogues. If an impurity is used as the print molecule, then the so-formed polymer thus comprises an impurity selective absorption material and can be used to selectively absorb the impurity from a mixture containing it.

Usually one of two different approaches has been followed: (A) the print molecule is covalently but reversibly bound; or (B) the initial interactions between monomers and the print molecule are non-covalent. A summary of this methodology is given in Ekberg et al (Trends Biotech., 7, 1989, 92), Mosbach et al. (Biotechnology, Vol. 14, February 1996, 163–170), Ekberg & Mosbach "Molecular imprinting: a technique for producing specific separation materials" TIBTECH—April 1989(7) 92–96; Ye, Ramström & Mosbach "Molecularly Imprinted Polymeric Adsorbents for By-product Removal" Anal. Chem. 1998(70) 2789–2795; Ramström, Ye, Krook & Mosbach "Screening of a combinatorial steroid library using molecularly imprinted polymers" Anal.

Comm. January 1998(35) 9–11; WO-A-93/05068; WO-A-9807671; WO-A-99/33768; EP-A-0 602 154. The contents of these documents are herein incorporated by reference.

The present invention therefore provides, in a first aspect, a process for the preparation of clavulanic acid or a pharmaceutically acceptable salt thereof in a purer form which comprises:

(i) contacting impure clavulanic acid with an impurity selective adsorption material;

(ii) separating the selective adsorption material with adsorbed impurity from the clavulanic acid.

The impurity selective adsorption material is preferably specific for an impurity known or suspected to be present in crude clavulanic acid, particularly succinyl tyrosine. The impurity selective adsorption material is preferably a molecularly imprinted polymer having specificity for a print molecule being such an impurity.

Suitably such a molecularly imprinted polymer may be a polymer formed by polymerisation of one or more functionally substituted monomer which binds to the impurity, in the presence of a cross-linking monomer and the print molecule.

Suitable polymers are those based on polyacrylate or polyacrylamide based systems, although polystyrene based systems may be used. Typical functionally substituted monomers used include carboxylic acids, sulphonic acids and heteroatomic bases, and particularly vinylic compounds, i.e. compounds which include a vinyl group $(CR^1R^2\!=\!CR^3\!-\!)$ where for example each of $R^1$, $R^2$ and $R^3$ is independently selected from hydrogen or $C_{1-8}$ alkyl, but preferably hydrogen. Examples of vinylic acids include vinylic mono- or di-carboxylic or sulphonic acids such as maleic acid, acrylic acids, e.g. alkylacrylic and fluoroalkylacrylic acids, typically $C_{1-5}$ allyl or fluoroalkyl, particularly acrylic acid itself, methylacrylic acid, or trifluoro-methylacrylic acid; itaconic acid, optionally substituted vinylbenzoic acids such as 4-vinylbenzoic acid, 4-vinylbenzyl-iminodiacetic acid, or acrylamido-2-methyl-1-propane sulphonic acid. Examples of heteroatomic bases include vinyl-substituted amino-, ammonium or amidine compounds, vinyl-substituted 5- or 6-membered nitrogen heterocycles such as vinylimidazoles, for example 1-vinylimidazole, 4(5)-vinylimidazole, vinylpyridines for example 2-vinylpyridine and 4-vinylpyridine. Further examples of such compounds include allylamines, 2-(diethylamino)ethyl methacrylate, 1-(2-aminoethyl)-methacrylamide, 2-(trimethylamino)ethyl methacrylate, N,N'-diethyl-4-styrylamidine, and urocanic acid $C_{1-5}$ alkyl esters such as the ethyl ester (formulae of these compounds are shown in FIG. 3). Typically two or more such functionally substituted monomers are used.

The print molecule may for example be a molecule which is known or believed to be an impurity in crude clavulanic acid. Examples of such impurities include those listed in Pharmeuropa (Vol. 12, No. 3, July 2000) which shows, inter alia, the following degradation products: pyrazine-2,5-diyl (diethanol), 3-[3,6-di(2-hydroxy-ethyl)pyrazin-2-yl]propanoic acid, 3-ethylpyrazin-2,5,diyl(diethanol) and 4-(2-hydroxyethyl)pyrrole-3-carboxylic acid.

A further impurity that may be formed during the culturing of the micro-organism is succinyl tyrosine, that is to say, the compound of formula (II):

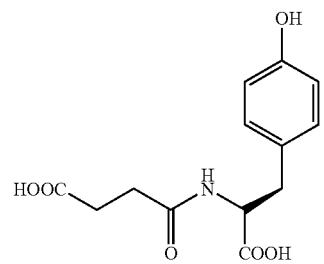

(II)

The term "succinyl tyrosine" used herein includes all isomers thereof.

It has been found that good molecularly imprinted polymers may be obtained for this impurity where at least one functionally substituted monomer utilised contains an appropriate positively charged moiety, which can interact with the functional groups of succinyl tyrosine. Suitable positively charged moieties include quaternary ammonium groups of formula $[N.R^1.R^2.R^3.R^4]^+$, where at least one, preferably three, of $R^1$, $R^2$, $R^3$ or $R^4$ is independently selected from hydrogen or $C_{1-8}$, preferably $C_{1-5}$, alkyl, especially methyl, and at least one, preferably only one, of $R^1$, $R^2$, $R^3$ or $R^4$ is independently selected from a polymerisable functional group, preferably a vinylic group, especially a vinylbenzyl group. The polymerisable group in such a moiety can polymerise to form the polymer, for example together with another polymerisable monomer such as those mentioned above. Suitably such a moiety can be provided in the form of a functionally substituted monomer being a salt of the positively charged group with a suitable counter anion such as a halide ion. A preferred example of such a functionally substituted monomer is vinylbenzyl trimethylammonium chloride.

A high degree of cross-linking is desirable for achieving the requisite specificity of the formed molecularly imprinted polymer. Suitable cross-linking agents possess one or more polymerisable double bond(s). Typical cross-linking agents used in molecular imprinting techniques include isomers of divinylbenzene (particularly for cross-linking of polystyrene based systems), e.g. 4-divinylbenzene, ethylene glycol dimethacrylate (EDMA), which is preferred, and trimethylolpropane trimethylacrylate (TRIM), and acrylamides such as N,N'-methylene-bisacrylamide, N,N'-phenylene-bisacrylamide and 2,6-bisacrylamidopyridine. Other cross-linking agents include tri- and tetra-functional acrylate cross-linkers such as pentaerytiritol triacrylate, and pentaerythritol tetraacrylate (particularly for peptide-selective molecularly imprinted polymers). A key factor affecting the choice of cross-linking agent is the solubility of the agent in the pre-polymeric solution. More than one cross-linking agent may be utilised.

A preferred molecularly imprinted polymer suitable for use in the process of this invention is therefore a polymer formed by polymerising a mixture of methylacrylic acid, vinylbenzyltrimethylammonium chloride or less preferably vinyl pyridine, and a cross-linking monomer, particularly ethyleneglycol dimethacrylate, in the presence of succinyl tyrosine.

Typically the molecularly imprinted polymer may comprise a polymer of a mixture of one or more functionally substituted monomer and cross-linker, with a composition (based on the starting materials) molar ratio cross-linker: monomer in the range 1:0.1–2.0, for example 1:0.1–0.5, suitably ca. 1:0.3. These molar ratios for example take into account that some cross-linkers, for example TRIM, have more than two polymerisable bonds. However a molar ratio funcional monomer: TRIM of ca. 1:1 may be suitable.

The above-mentioned preferred molecularly imprinted polymer may comprise a polymerised mixture of methylacrylic acid, vinylbenzyltrimethylammonium chloride, and ethyleneglycol dimethacrylate, with a composition (based on the starting materials) ratio ethyleneglycol dimethacrylate:vinylbenzyltrimethylammonium chloride:methylacrylic acid in the range 1:0.2:0.1+/−10%.

The molecularly imprinted polymers for use in this invention may be prepared according to procedures known to those skilled in the art of molecular imprinting, for example see WO-A-94/11403 or WO-A-97/38015 or Ranström et. al "Artificial antibodies to corticosteroids prepared by molecular imprinting" Chem. Biol. (1996)3:471-477.

The whole molecular imprinting procedure is normally carried out in a solvent (also described as a porogen) which, inter alia, governs the strength of the interactions between print molecule and monomers. In addition, the choice of solvent also influences the morphology of the formed polymer. For instance, the more polar the solvent utilised the weaker may be the interaction between the print molecule and functional monomers. On the other hand, the solvent influence on the structure of the prepared may compensate for the apparent disadvantage of using the more polar solvent. Many common solvents are widely used in molecular imprinting techniques. Suitable example include water, acetonitrile, toluene, dichloromethane and methanol. Where used herein the term "solvent" or "porogen" includes both co-solvent and single solvent systems. A preferred solvent for such a preparation is methanol.

The polymerisation of the monomers is typically carried out in the presence of an initiator or initiating agent. A suitable example of such an agent is azobis-isobutyronitrile (AIBN). More than one initiator may be utilised.

It will be appreciated from the above, that the choice of functional monomers, solvent system and cross-linker reagent to be used for the production of a specific adsorption material, are inter-related. Thus, optimum conditions may be determined by the person skilled in the art of molecular imprinting using standard methods and without undue experimentation.

The polymerisation typically results in a solid mass of the molecularly imprinted polymer, which can be broken down into particles of a suitable size by appropriate mechanical processes, e.g. grinding, sieving and repeated sedimentation, e.g. in acetone. A suitable particle size will depend upon the way in which the polymer is subsequently used, but 10–25 microns has been found suitable. The print molecule may be removed from the polymer by for example slurry packing the polymer particles in a column and washing with a suitable solvent, extraction of the print molecule being monitored appropriately, typically by HPLC. Thereafter the polymer particles may be removed from the column, washed, e.g. with acetone, and dried, e.g. under vacuum.

The invention further provides for a process for the preparation of a selective adsorption material which comprises:
(a) contacting a print molecule being a known impurity of clavulanic acid with at least one functionally substituted monomer, preferably a plurality of functionally substituted monomers, in a solvent system;
(b) polymerising said monomer(s) in the presence of a cross linking agent;
(c) removing the print molecule from the so-formed polymer by extraction.

The invention further provides for a selective adsorption material obtainable by the above process.

The invention further provides a selective adsorption material, typically a molecularly imprinted polymer, for use in the purification of a clavulanic acid or a pharmaceutically acceptable salt thereof.

The selective adsorption materials prepared in accordance with this invention are highly resistant to physical (e.g. stress, high temperatures and pressures) and chemical factors (e.g. resistance to treatment with acid, base and wide range of organic solvents and aqueous medium). The selective adsorption material can be re-used many times, up to 100 times, without significant reduction in utility. The selective adsorption material may for example be re-generated after use by the same procedure as is used to remove the print molecule from the polymer after its initial preparation.

It will be appreciated that an impurity specific selective adsorption material prepared in accordance with this invention can be utilised to remove that particular impurity from any other system e.g. fermentation broth which comprises a plurality of chemical species i.e. is not limited to a system comprising clavulanic acid. Thus, a succinyl tyrosine selective adsorption material prepared in accordance with this invention could be used to selectively remove this species from other system in which succinyl tyrosine is present. For example the impurity selective adsorption material could also be used to remove the impurity from a salt or compound of clavulanic acid containing the impurity, for example if prepared from impure clavulanic acid itself. For this reason the term "impure clavulanic acid" used herein includes such an impure salt or compound of clavulanic acid.

In the process of this invention, contacting of the impure clavulanic acid with the impurity selective adsorption material, e.g. the above described molecularly imprinted polymer, may be carried out in a suitable solvent. Because of the sensitivity of clavulanic acid to water an organic solvent is preferred. Methanol is found to be a useful solvent. As mentioned above a common procedure for isolation of clavulanic acid involves extraction into an organic solvent, and the contacting of the impure clavulanic acid with the impurity selective adsorption material may be done using a solution of clavulanic acid obtained in this procedure. Typical solvents used for extraction are methylisobutyl ketone and ethyl acetate. If solvents such as these latter are used, then to reduce the possibility of clavulanic acid itself binding to the polymer it can be desirable to increase the polarity of the solvent, for example by mixing such a solvent with a more polar solvent such as methanol, and mixtures comprising 1:1 methylisobutylketone:methanol have also been found to be useful. The process may be performed with clavulanic acid solutions of typical concentrations as obtained by such extraction procedures, and typically the clavulanic acid and impurity selective adsorption material may be contacted over a period of up to five hours, more typically up to two hours, although suitable contact times may be determined experimentally. Suitably a solution of impure clavulanic acid can be continuously circulated into contact with the impurity selective adsorption material, with monitoring of the impurity levels, until a satisfactory level of purification is achieved.

Thereafter the solution of purified clavulanic acid in the organic solvent may be further processed in a known manner, for example back-extracted into an aqueous phase e.g. in the form of an amine or metal salt, or for example converted into a metal salt without back extraction.

The process of the invention may form part of an overall process for the preparation of a pharmaceutically acceptable salt of clavulanic acid in a purer form, starting from crude clavulanic acid e.g. as formed in a fermentation broth. Such an overall process may, for example, comprise (a) fermentation of a micro-organism which produces an aqueous broth containing clavulanic acid;
(b) extraction of the clavulanic acid into an organic solvent;
(c) conversion of the clavulanic acid to a pharmaceutically acceptable salt of clavulanic acid; and contacting the clavulanic acid with a selective adsorption material for a known impurity at any point in the above overall process, but preferably subsequent to step (b).

One form of such a process includes a step following step (b), comprising a step (d) involving preliminary conversion of the clavulanic acid into an intermediate amine salt of clavulanic acid, which is subsequently converted to the pharmaceutically acceptable salt.

It will be further appreciated that a plurality of impurity specific selective adsorption materials may be necessary to remove a plurality of known impurities from clavulanic acid. In such circumstances, the impurity specific selective adsorption materials may be contacted with the impure clavulanic acid at different points in the overall process.

Preferably the process of this invention may form part of an overall process for the preparation of a preferred pharmaceutically acceptable salt being potassium clavulanate. A preferred amine salt formed in step (d) above is the tertiary butylamine salt of clavulanic acid. This can be prepared by reaction of tertiary butylamine with clavulanic acid, and easily isolated as an acetone solvate. Both the tertiary butylamine salt and its acetone solvate can readily be converted into potassium clavulanate. Such procedures are disclosed in EP-A-0 026 044, the contents of which are hereby incorporated by reference. Other suitable amine salts are disclosed in the references cited above.

Alternatively, the process may form part of an overall process in which a pharmaceutically acceptable salt of clavulanic acid, e.g. potassium clavulanate is formed directly, that is to say, isolated from solution as a solid without conversion to an amine salt. Such a method is described in WO-A-95/21173, the contents of which are hereby incorporated by reference, and which is to be taken as illustrative rather than by limitation.

The following examples illustrates the preparation of a impurity specific selective adsorption material according to this invention along with its utility in the process of this invention.

Figure 1:
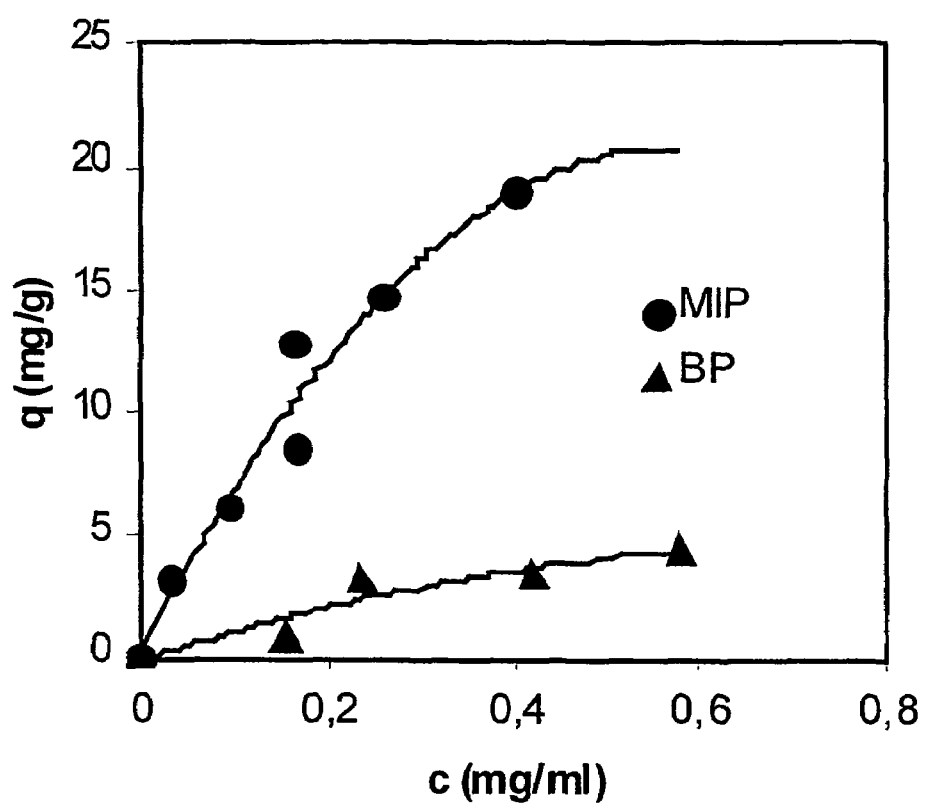
FIG. 1 shows the adsorption binding isotherm of succinyl tyrosine for molecularly imprinted polymer (MIP) and blank polymer (BP).

1. PREPARATION OF A MOLECULARLY IMPRINTED POLYMER ("MIP") FOR THE SELECTIVE REMOVAL OF SUCCINYL TYROSINE FROM CLAVULANIC ACID

Succinyl tyrosine (0.4 mmol), vinylbenzyl trimethylammonium chloride (1.6 mmol), methylacrylic acid—MAA (0.8 mmol), ethyleneglycol dimethacrylate—EDMA (8 mmol) and 50.0 mg AIBN were dissolved in 4.0 ml methanol. The obtained solution was purged with nitrogen for 5 minutes. Polymerisation was thermally induced at 60° C. and the reaction continued for 16 hours. The polymer monolith obtained was ground in a mechanical mortar, particles with diameter of 10–25 μm collected by repetitive grinding, sieving and sedimentation in acetone. To remove the print molecule, polymer particles were packed into a stainless steel column and washed with methanol-acetic acid (9:1, v/v) using an HPLC solvent delivery system for 18 hours at a flow rate of 1.0 ml/min. For batch mode experiments, the washed particles were removed from the column, re-suspended in acetone for several times and dried under vacuum.

Using an identical procedure a molecularly imprinted polymer was prepared using 4-vinylpyridine (1.6 mmol) in place of the vinylbenzyl trimethylammonium chloride.

Non-molecularly imprinted control "blank" polymers ("BP") were also prepared using identical procedures but without the print molecule.

2. CHROMATOGRAPHIC ANALYSIS OF MOLECULARLY IMPRINTED POLYMERS

Polymer particles were suspended in acetone and packed into a standard HPLC column (100×4.6 mm). Chromatographic analyses were performed using a LaChrom L-7100 solvent delivery system, and a L-7455 diode array detector (Merck, Germany). Acetonitrile or methanol containing 0.5 or 1.0% acetic acid was used as the mobile phase at a flow rate of 0.5 or 1.0 ml/min. The analytes were monitored at 280 nm. Acetone was used as a void marker. Capacity factor (k') was calculated as $(t-t_0)/t_0$, where t is the retention time of the analyte and $t_0$ is the retention time of the void marker. Imprinting effect was evaluated by the imprinting factor ($I=k'_i/k'_B$), where $k'_i$ and $k'_B$ are the capacity factors of the MIP and the BP, respectively.

Using the vinylbenzyl trimethylammonium chloride-based MIP a strong ionic interaction with succinyl tyrosine was found, resulting a good imprinting effect (I=2.18) in methanol: acetic acid (99:1 V/V, flow rate 1.0L/min). Using the 4-vinylpyridine-based MIP a weaker interaction with succinyl tyrosine was found resulting a moderate imprinting effect (I=1.75) in the weaker eluant acetonitrile: acetic acid (99.5:0.5 V/V, flow rate 0.5L/min). The vinylbenzyl trimethylammonium chloride-based MIP was therefore used for the subsequent experiments described below.

3. DETERMINATION OF ADSORPTION ISOTHERMS

Adsorption experiments were performed by adding MIP or BP (50.0 mg) into 1.0 ml of previously prepared succinyl tyrosine solution in methanol at different concentrations. The suspension was incubated on a rocking table at room temperature for 1 hour. After centrifugation, the amount of free (unbound) succinyl tyrosine in the supernatant was determined by reverse phase chromatography (C-18 column, mobile phase 0.1% TFA in 5% MeCN) with a flow rate of 0.25 ml/min at 40° C.

FIG. 1 shows the adsorption binding isotherm of succinyl tyrosine for molecularly imprinted-polymer (MIP) and blank polymer (BP).

The adsorption isotherms show that the BP only adsorbed a very small amount of succinyl tyrosine, and the adsorption curve represents typical non-specific binding. Under saturation conditions the vinylbenzyl trimethylammonium chloride-based MIP bound ca 10 times more succinyl tyrosine than the BP.

4. SUCCINYL TYROSINE REMOVAL FROM A CLAVULANIC ACID FERMENTATION PRODUCT

A batch mode test and a flowing ("dynamic") mode test were carried out.

Batch Mode Test:

50 mg vinylbenzyl trimethylammonium chloride-based MIP was incubated with 1.0 ml of succinyl tyrosine solution (0.3 mg/ml) in the presence (spiked) and absence (unspiked) of 15 mg/ml of clavulanic acid for 1 h at room temperature. Samples were centrifuged at 14,000 rpm for 10 minutes. The concentration of free succinyl tyrosine in the supernatant was quantified with reverse phase HPLC, from which the amount of bound succinyl tyrosine was calculated.

Flowing Mode Test:

40 ml of succinyl tyrosine solution (0.3 mg/ml) containing clavulanic acid (15 mg/ml) was circulated at a flow rate of 1.0 ml/min. through an HPLC column (250 mm×4.6 mm I.D.) for 1 hour at room temperature. The column was packed with either succinyl tyrosine specific vinylbenzyl trimethylammonium chloride-based MIP or the blank polymer After circulation, the solution was analysed with Reversed-phase HPLC.

Figure 2:
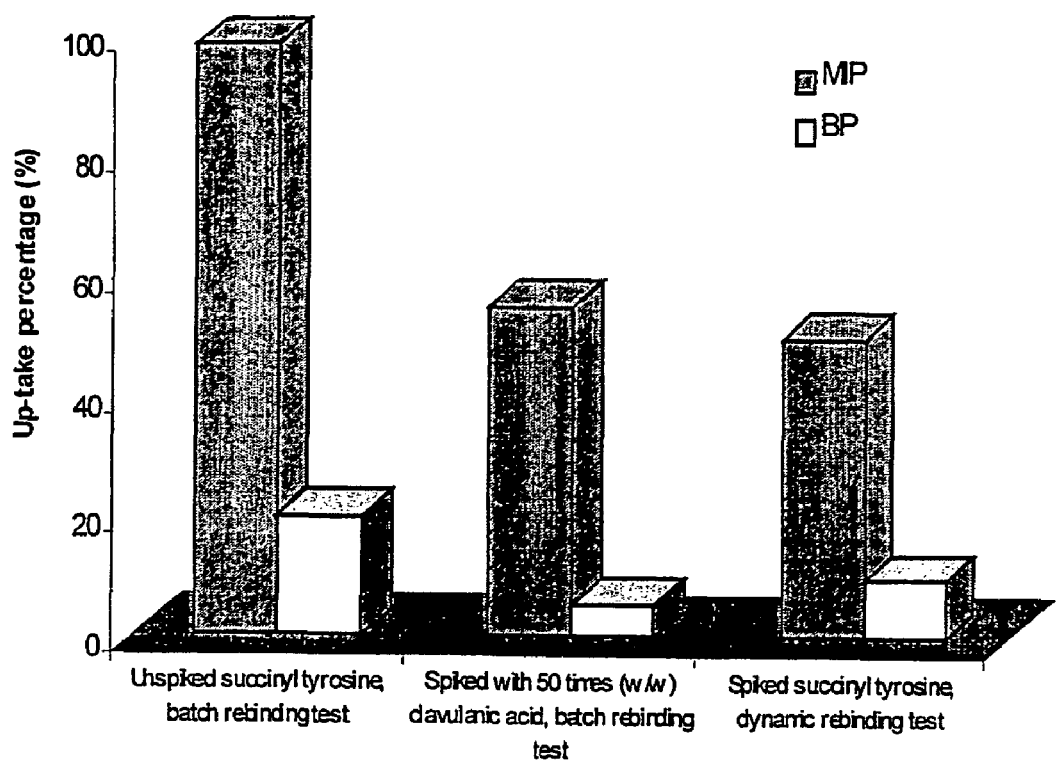
FIG. 2 shows a comparison of binding properties using an unspiked succinyl tyrosine sample and samples spiked with 50 times (w/w) clavulanic acid, using batch and flowing mode systems.
Figure 3:
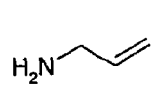
FIG. 3 shows formulae of some vinyl-substituted monomers.
Figure 3:
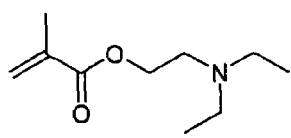
Figure 3:
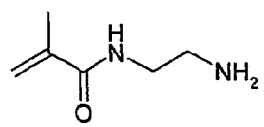
Figure 3:
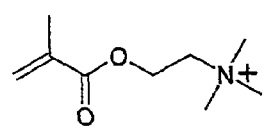
Figure 3:
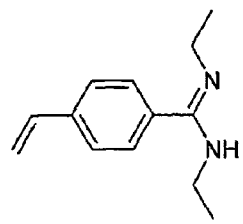
Figure 3:
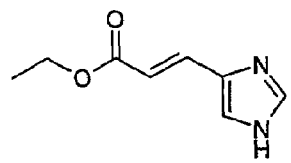

FIG. 2 shows a comparison of binding properties using an unspiked succinyl tyrosine sample and samples spiked with 50 times (w/w) clavulanic acid, using batch and flowing mode systems.

FIG. 2 shows that in the batch mode, in the presence of excess clavulanic acid the amount of succinyl tyrosine bound to the MIP was reduced by 40%, but this was still at least 5 times higher than the amount that bound to the BP. In the flowing mode with the same MIP load (ca. 50 mg polymer/ml sample solution) almost the same results were achieved as in the batch process—but with the advantage that the set up enabled easy regeneration of the polymer by circulation of a suitable solvent such as methanol.

The amount of clavulanic acid bound to the MIP and to the BP was also measured. With the MIP the purified clavulanic acid (recovery 97.6%) contained less than 1% of succinyl tyrosine, in contrast to the BP (recovery 93.5%) containing 1.7% succinyl tyrosine.

5. SOLVENT EFFECTS

Using methylisobutylketone: methanol (1:1 v/v) as a solvent it was found that vinylbenzyl trimethylammonium chloride-based MIP selectively bound succinyl tyrosine with a capacity of 64.2 mg/g and a dissociation constant of 0.16 mM.

These data indicate that a selective adsorption material for a known impurity of clavulanic acid can be readily prepared and utilised to selectively remove this selected impurity from a large excess of clavulanic acid.

The invention claimed is:

1. A process for the preparation of clavulanic acid or a pharmaceutically acceptable salt thereof which comprises:
   (i) contacting impure clavulanic acid containing succinyl tyrosine as an impurity with an impurity selective adsorption material-wherein the impurity selective adsorption material is a molecularly imprinted polymer having specificity for succinyl tyrosine of formula (II); and

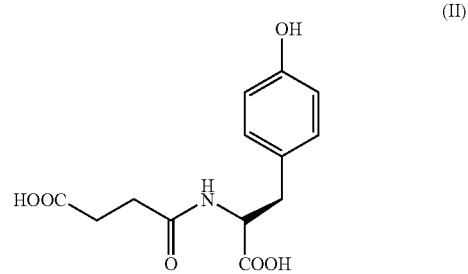

(ii) separating the selective adsorption material with succinyl tyrosine of formula (II) from the clavulanic acid, and optionally converting the clavulanic acid into a pharmaceutically acceptable salt thereof.

2. A process according to claim 1 wherein molecularly imprinted polymer comprises a polymer formed by polymerization of one or more functionally substituted monomer which contains a positively charged moiety which can interact with a functional group of succinyl tyrosine of formula (II).

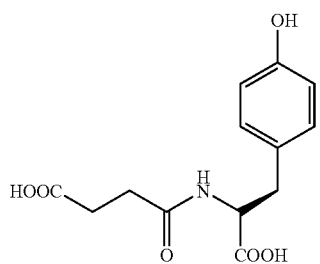

(II)

3. A process according to claim 2 wherein the positively charged moiety is a quaternary ammonium group of formula [N.R$^1$.R$^2$.R$^3$.R$^4$]$^+$, where at least one of R$^1$, R$^2$, R$^3$ or R$^4$ is independently selected from hydrogen or C$_{1-8}$ alkyl, and at least one of R$^1$, R$^2$, R$^3$ or R$^4$ is independently selected from a polymerisable functional group.

4. A process according to claim 3 wherein the molecularly imprinted polymer comprises a polymer formed by polymerization of vinylbenzyltrimethylammonium chloride.

5. A process according to anyone of claim 1, 2, or 3 wherein the molecularly imprinted polymer comprises a polymer formed from vinyl pyridine.

6. A process according to claim 1 wherein the molecularly imprinted polymer comprises a polymer formed by polymerizing a mixture of methylacrylic acid, vinylbenzyltrimethylammonium chloride or vinyl pyridine, and a cross-linking monomer, in the presence of succinyl tyrosine of formula (II).

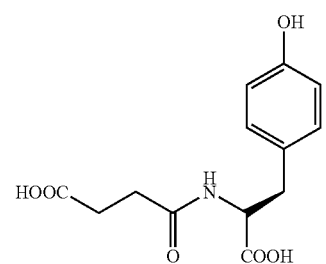

(II)

* * * * *